United States Patent [19]
Schnurer et al.

[11] Patent Number: 5,724,982
[45] Date of Patent: Mar. 10, 1998

[54] APPARATUS AND METHOD FOR MEASURING FLUID FLOW

[75] Inventors: John Herman Schnurer, Yellow Springs; Robert F. Freund, Waynesville, both of Ohio

[73] Assignee: Modern Technologies Corp., Dayton, Ohio

[21] Appl. No.: 485,737

[22] Filed: Jun. 7, 1995

Related U.S. Application Data

[63] Continuation of Ser. No. 168,637, Dec. 16, 1993, Pat. No. 5,439,003.

[51] Int. Cl.[6] ................................................ A61B 5/026
[52] U.S. Cl. ...................... 128/692; 128/668; 73/861.009
[58] Field of Search ............................... 128/691–692, 128/693–694, 668, 713; 73/861.08–861.09

[56] References Cited

U.S. PATENT DOCUMENTS

| | | | |
|---|---|---|---|
| 2,913,386 | 11/1959 | Clark, Jr. | 204/195 |
| 3,242,729 | 3/1966 | Keller | 73/194 |
| 3,773,037 | 11/1973 | Koln | 128/692 |
| 3,823,706 | 7/1974 | Davis | 128/691 |
| 3,930,493 | 1/1976 | Williamson | 128/692 |
| 4,156,364 | 5/1979 | Hill | 73/194 |
| 4,166,455 | 9/1979 | Findl et al. | 128/691 |
| 4,220,045 | 9/1980 | Suzuki et al. | 73/861 |
| 4,248,086 | 2/1981 | Zizine | 73/861 |
| 4,331,037 | 5/1982 | DuVall | 73/861 |
| 4,967,753 | 11/1990 | Haase et al. | 128/662 |
| 5,031,632 | 7/1991 | Watanabe | 128/691 |
| 5,059,851 | 10/1991 | Corl et al. | 310/334 |
| 5,078,148 | 1/1992 | Nassi et al. | 128/661.09 |
| 5,121,749 | 6/1992 | Nassi et al. | 128/692 |
| 5,125,137 | 6/1992 | Corl et al. | 29/25.35 |
| 5,439,003 | 8/1995 | Schnuer et al. | 128/692 |

FOREIGN PATENT DOCUMENTS

| | | |
|---|---|---|
| 2463369 | 2/1981 | France . |
| 3906998 | 9/1990 | Germany . |
| 4034163 | 5/1991 | Germany . |
| 4117912 | 12/1992 | Germany . |

OTHER PUBLICATIONS

E. Bleuler et al., *Electronic Methods*, Academic Press, New York, 1964, pp. 558–579.

*Primary Examiner*—Robert L. Nasser
*Attorney, Agent, or Firm*—Jacox, Meckstroth & Jenkins

[57] ABSTRACT

A method and apparatus for measuring the flow rates of fluids is disclosed. The apparatus comprises a probe which may be placed in a fluid inside a vessel, such as a blood vessel. The probe comprises at least one pair of conductors to which the circuit provides a small current. As ions are disordered or migrate between at least one of the conductors and the fluid, a current or charge is caused to flow between the conductors. The circuit measures this current using a differential amplifier and generates an output signal corresponding thereto. The output signal is then displayed on a monitor. Because the current flow is closely related to the rate of flow of the fluid past the probe, an accurate measurement of the flow rate is obtained.

8 Claims, 5 Drawing Sheets

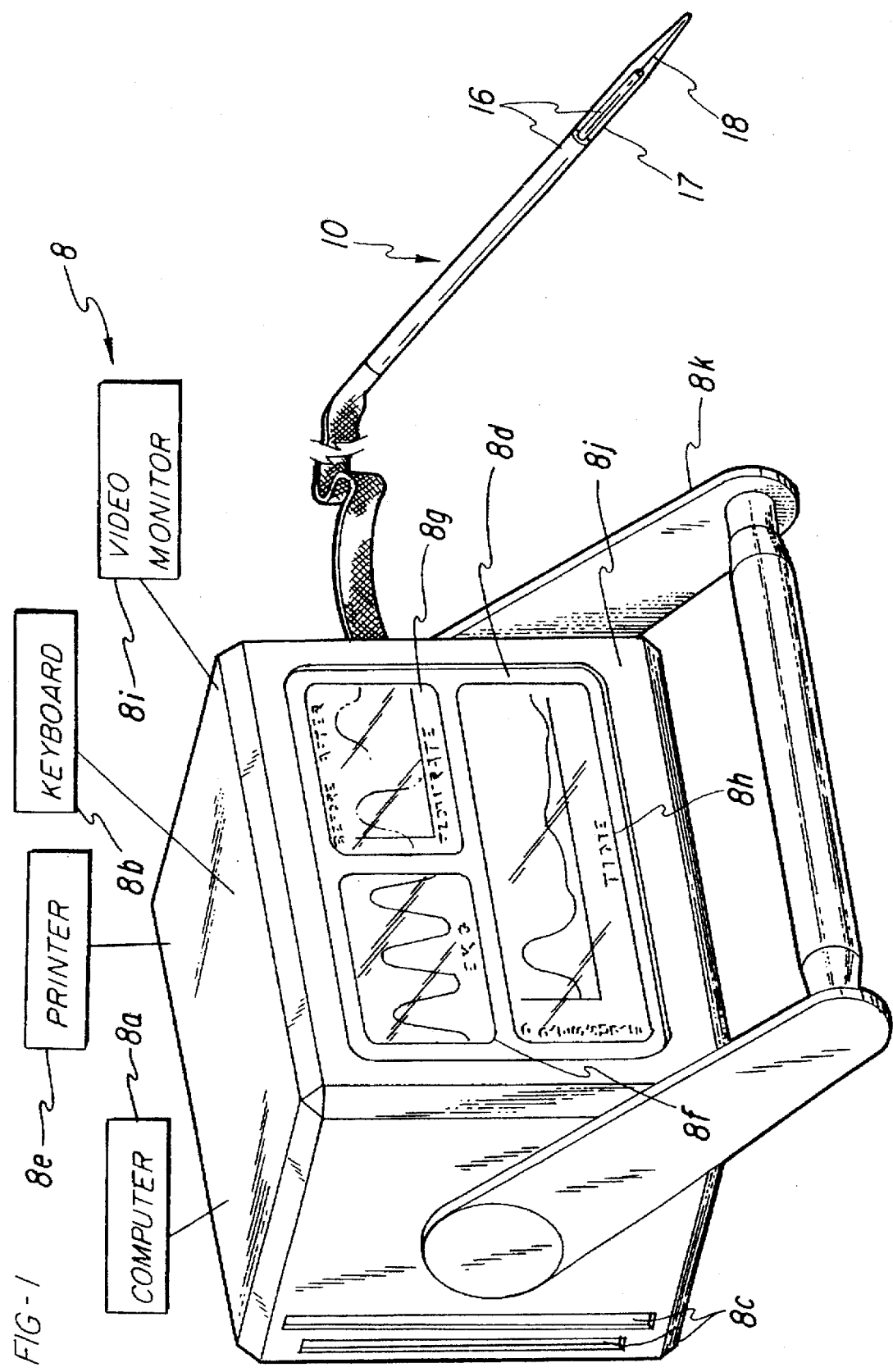

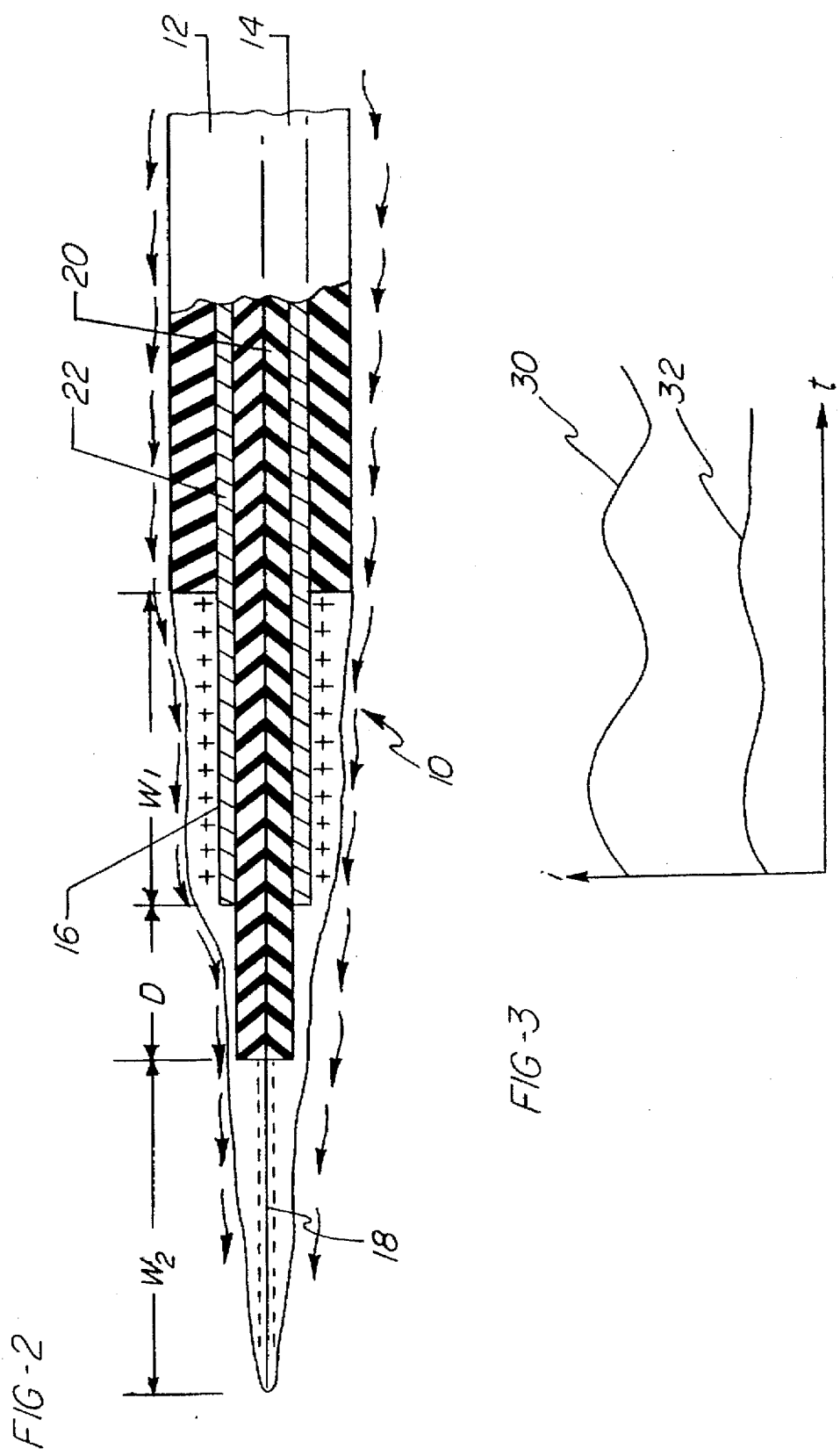

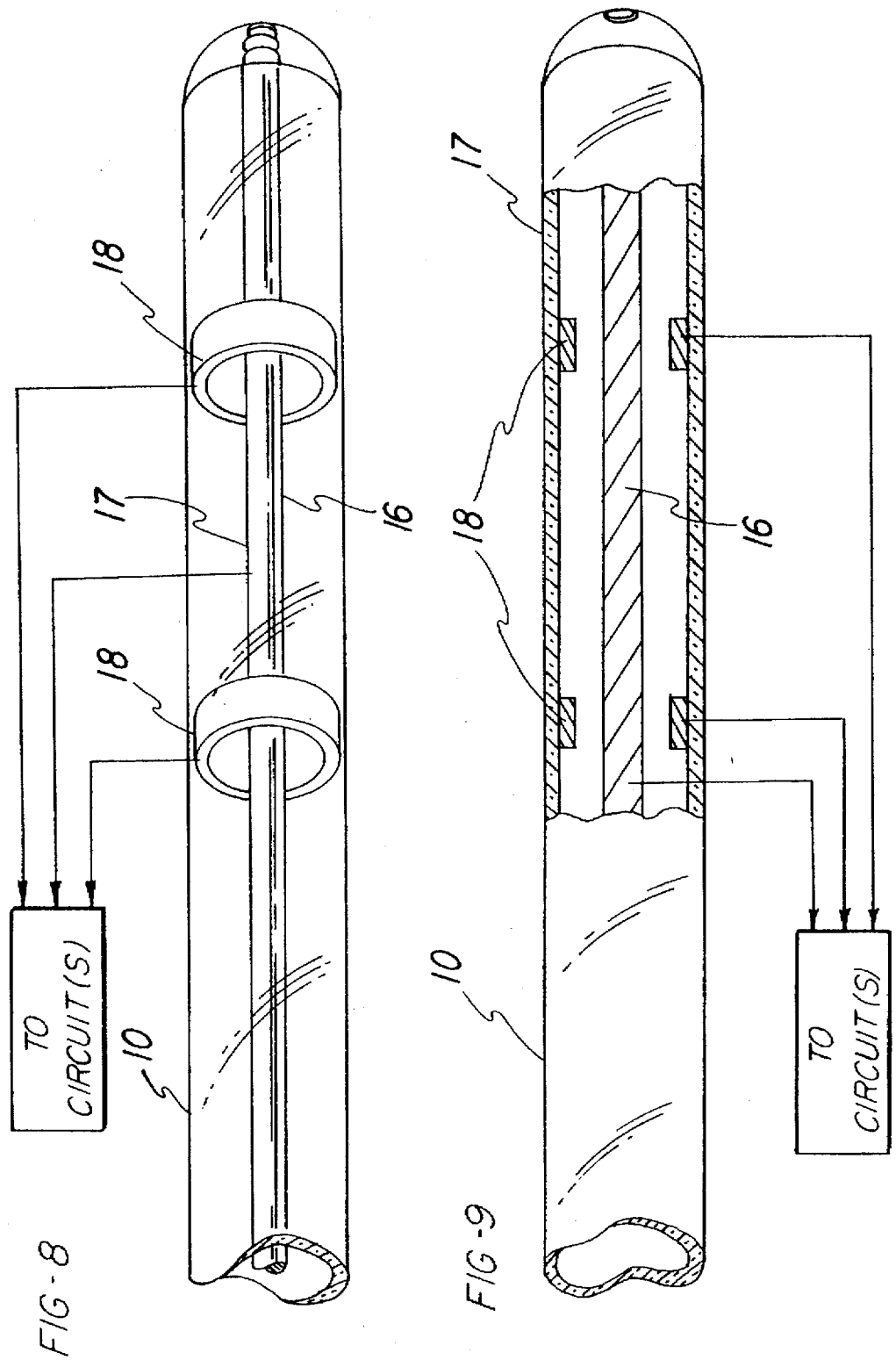

APPARATUS AND METHOD FOR MEASURING FLUID FLOW

RELATED APPLICATION

This application is a Continuation of application Ser. No. 08/168,637 filed Dec. 16, 1993, now U.S. Pat. No. 5,439,003.

BACKGROUND OF THE INVENTION

1. Field of the Invention

This invention relates to a method and apparatus for measuring the flow rate of a fluid and, more particularly, to an apparatus and method for measuring fluid flow rate in a vessel by monitoring the movement of ions between at least one of a plurality of conductors and the fluid.

2. Description of Related Art

Diagnostic catheters have heretofore been provided measuring intravascular pressure and blood flow using thermal dilution, dye dilution and oxygen consumption methods. Intravascular catheters have also been developed which measure instantaneous flow velocity utilizing ultrasonic Doppler transducers to measure the "Doppler shift" created by movement of red blood cells, acting as targets, with the blood vessel or organ to which a measurement is being made. Doppler systems of the past typically used Doppler catheters which were only useful for the measurement of flow velocity within a small sample volume contained within the blood vessel of interest.

Other methods, systems and apparatuses have been designed to measure flow rate using ultrasonic techniques. For example, U.S. Pat. No. 5,174,295 discloses a system for measuring characteristic of flow of liquid in a vessel of a patient comprising a transducer positioned in a vessel in a patient of supplying ultrasonic energy. The transducer produced a substantially uniform beam which encompassed the vessel. The transducer received ultrasonic energy back scattered from the plasma and red blood cells and provides an electrical output signal which was detected by a detector which generated a moment signal in response thereto. The signal was then normalized to provide an output characteristic of the flow of the liquid in the vessel.

A disadvantage of the ultrasonic systems of the past was that they required relatively high driving voltages. Another disadvantage is that they were often complex in design and it was sometimes difficult to maintain stability. For example, in ultrasonic systems which use coaxial cable, the coaxial cable is possessed of capacitance. In general the smaller the overall diameter of the cable, the higher its capacitance. Cable capacitance tends to attenuate high frequency AC signals. As cable capacitance increases, the attenuation increases and this attenuation can become significant as cable diameters become smaller and smaller, such as would be required for use with a catheter. This attenuation is undesirable. In addition, these systems typically used a cable having a fairly large capacitance. The impedance and capacitance often adversely affected the signal-to-noise ratios which, in turn, affected the ultimate flow reading.

As mentioned above, thermal dilution devices have also been used to measure fluid flow rates. In general, these devices provided a thermal conductor, such as a thermistor, which was energized with a current to cause the thermal conductor to be set at a desired temperature. As fluid flowed past the thermistor, heat was dissipated by the fluid. Additional current was supplied to the thermistor to maintain the temperature of the thermistor at a predetermined level. The change in additional current was then measured, thereby providing an indication of the flow rate of the fluid. To maintain the current levels needed, the thermal dilution device often required voltage input levels of, for example, 1.5 volts at 30 milliamps for 0.045 watts heating at the thermistor site.

A problem with the thermal dilution devices of the past is that they tended to be slow in measuring flow rate. In addition, sometimes their accuracy depended in large part on the mass of the thermal conductor. Finally, they also typically required relatively high current levels to cause the temperature of the thermal conductors to be maintained at the desired temperature.

Still another problem with flow measuring instruments of the past is that they were not typically multifunctional in that they were not typically designed with other sensing apparatus. For example, they did not include an optical sensor for visual inspection in conjunction with flow measuring. Also, they were not typically used with balloon catheters of the type used in heart catheterization procedures.

What is needed, therefore, is a measuring device, method and system which overcomes the problems of the prior art and which provides an accurate, yet relatively inexpensive way to measure the flow rate of a fluid, like blood, and which can be used in conjunction with other instruments or equipment (such as optical sensors or balloon catheters).

SUMMARY OF THE INVENTION

It is, therefore, a primary object of this invention to provide a measuring device for measuring the flow rate of a fluid, such as blood, by measuring the movement of ions between at least one conductive surface and the fluid using a micro current or small amount of current flow.

In one aspect, this invention comprises a method for measuring the flow rate of a moving fluid, said method comprising the step of: generating a signal corresponding to the transfer of charge between a pair of conductors positioned in said fluid.

In another aspect, this invention comprises a method for measuring the amount of blood flow in a vessel having an occlusion; the method comprises the steps of: placing a probe having at least one conductive set near the occlusion; and generating a signal corresponding to the dissipation of ions from at least one of the conductors as the blood flows past the conductor.

In still another aspect, this invention comprises a flow meter for measuring flow in a vessel comprising: a probe having a plurality of conductors; a circuit coupled to said plurality of conductors for generating a signal corresponding to the dissipation of ions on at least one of said plurality of conductors as fluid flows past said probe; and a display coupled to said circuit for receiving said signal and generating a display corresponding thereto.

Another object of this invention is to provide a method and apparatus which can measure flow in a vessel using a controlled or servo controlled current source of 10 microamperes or less.

Another object of this invention is to provide a method and apparatus which is easy to use and which is not restricted to measuring the flow rate of blood.

Still another object of this invention is to provide a method and apparatus which inexpensive to manufacture.

An advantage of this invention is that it provides a method and apparatus that can measure fluid flow in a vessel using a relatively small amount of current.

Another advantage of this invention is that it provides an apparatus and method which is relatively simple in design relative to the flow measuring devices of the past.

Still another advantage is that it is relatively easy to use and inexpensive to manufacture when compared to flow measuring devices of the past, such as the Doppler devices mentioned above. Further, it facilitates the use of cables having relatively high capacitance.

Yet another advantage of the invention is that it may be used with other types of instruments, or equipment, such as balloon catheters or optical sensors.

These objects, advantages and features of the invention will become apparent from a reading of the following description, drawing and claims.

BRIEF DESCRIPTION OF THE DRAWING

FIG. 1 is a view of a flow meter according to one embodiment of the invention;

FIG. 2 is a fragmentary view of a probe, showing the electrical charge associated with a pair of conductors;

FIG. 3 are illustrative voltage waveforms showing voltage being proportional to a current flowing through a vessel;

FIG. 8 is another view of a probe having two conductors and of a common ground; and FIG. 9 is a schematic view of the probe shown in FIG. 8.

DESCRIPTION OF THE PREFERRED EMBODIMENT

Figure 4:
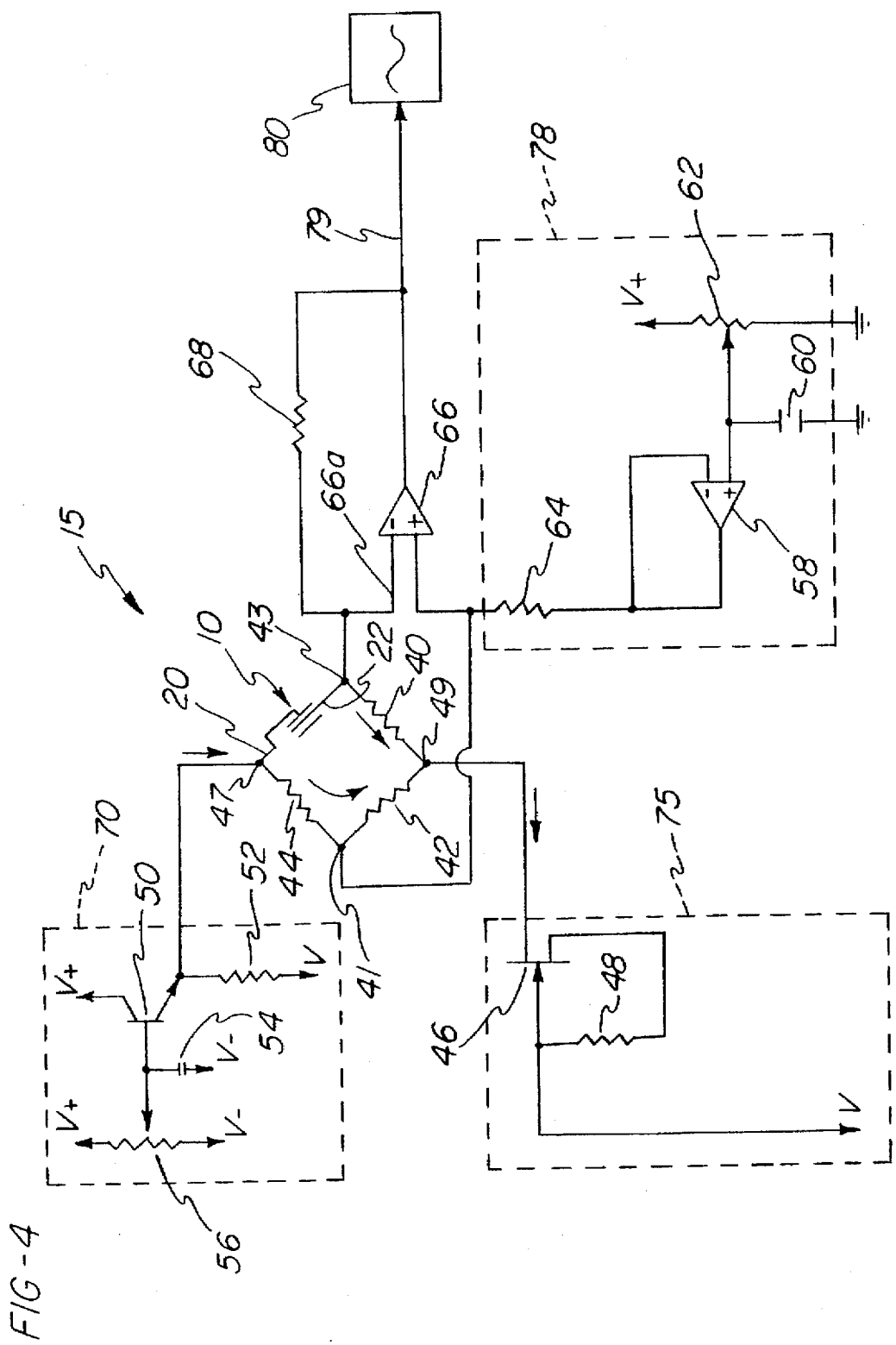
FIG. 4 is a schematic of a circuit used in one embodiment of the invention.

Referring now to FIG. 1, a flow meter 8 according to one embodiment of the invention is shown. The flow meter 8 comprises a probe 10 which senses or measures the actual flow rate of a fluid.

As best shown in FIG. 1, flow meter 8 comprises a computer 8a having software (not shown) which is capable of processing information inputted to the computer 8a. In this regard, information may be input into a computer 8a in a number of conventional manners, including through a keyboard 8b, through disc drives 8c, or through an interactive screen, touch screen, stylus, digitizer or other input device, including display 8d. The computer 8a in the flow meter 8 can output information in any conventional manner, such as through a printer 8e, disc drives 8c, display 8d, or video monitor 8i.

It is to be noted that the software in computer 8a, which enables flow meter 8 to process data and generate a plurality of output images, such as images 8f, 8g, and 8h. For example, computer 8a can process data such that a display 8d shows a graphical representation of an EKG (8f), a graphical presentation of a flow rate (8g), proximal and distal of an occlusion in the vessel 11, and a graphical representation (8h) of pressure in vessel 11 over time (such as before, during and after angioplasti procedures). Thus, it should be apparent that flow meter 8 comprises software and hardware which is capable of producing a variety of flexible displays in a format which is easily selected by a user and which promotes greater utility and ease of use, thereby facilitating the ease of use of the flow meter 8.

Figure 7:
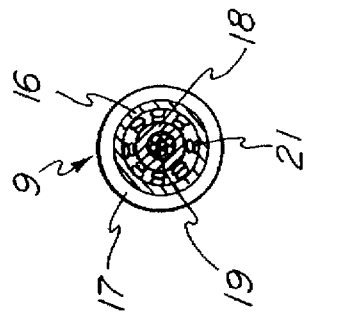
FIG. 7 is a sectional view taken along the line 7–7 in FIG. 6, showing the flow meter used with a balloon catheter.

In addition, the video monitor 8c displays a video image in response to an optical signal generated by an optical sensor which is described in more detail below in relation to FIGS. 6 and 7.

Figure 5:
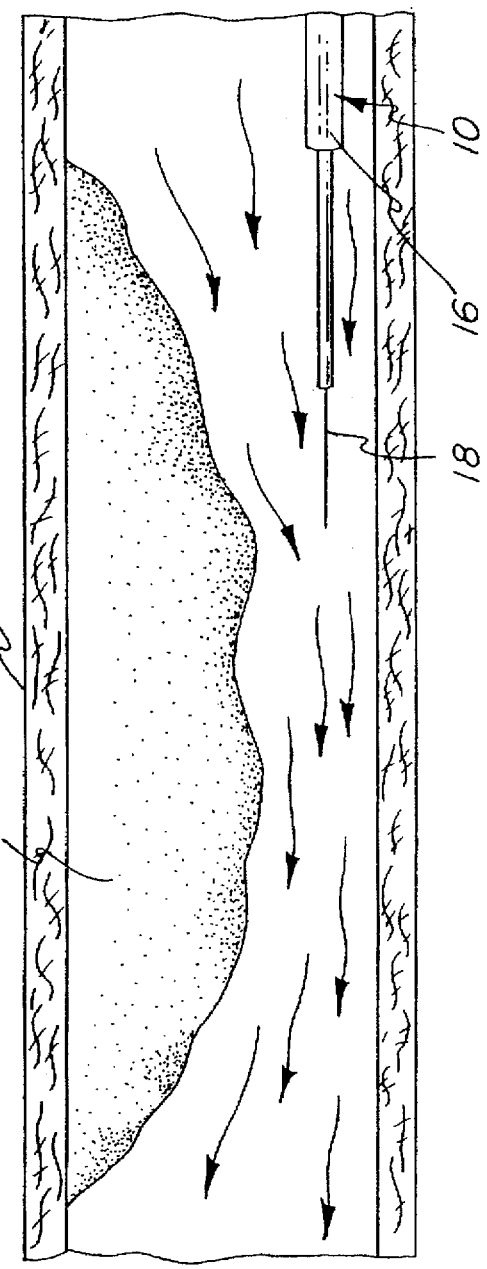
FIG. 5 is a sectional view showing a probe positioned relative to an occlusion in a vessel of a patient.

The probe 10 may be configured as generally illustrated in FIG. 2. As shown, probe 10 may be of a size appropriate for insertion into a vessel, such as a blood vessel 11 (FIG. 5). The probe 10 is of a size and configuration to permit movement through a vessel 11, for example, to a point of suspected occlusion 13 (FIG. 5). Probe 10 (FIG. 2) may comprise a dielectric sheath 12 fitted with a dielectric rod 14. A conductor or conductive wire 18 extends longitudinally through rod 14 and extends outwardly therefrom for surface contact with a fluid (for example, blood) flowing past the probe 10. A portion of the exposed surface of rod 14 is coated with another conductor or layer 16 of conductive material. Thus, layer 16 and wire 18 comprise a conductor set. As explained later herein, this conductive set may comprise more conductors if desired. Lead lines 20 and 22 are connected to wire 18 and layer 16, respectively, and ultimately to a circuit 15 (FIG. 4).

It is to be noted that the probe 10 may be provided with a protective coating 17 which protects wire 18 and layer 16, while permitting the migration or transfer of ions between one or both wire 18 and layer 16 and the fluid. The protective coating 17a may also be useful to provide an outer configuration which is easy to insert in vessel 11 and which will minimize or reduce damage to the vessel as it is being inserted therein. The protective coating 17 may be Teflon, amorphous glass, plastic or any suitable coating which does not prevent ionic migration between wire 18 and layer 16.

In the embodiment being described, layer 16 and wire 18 have a width W1 and W2, respectively, which are each on the order of about 4–8 mm wide (as viewed in FIG. 2). The layer 16 and wire 18 may be any size which is capable of carrying a small current of 10 microamperes of current or less. It should also be noted that the distance D (FIG. 2) between the wire 18 and layer 16 is approximately 4–8 mm in the embodiment being described.

In operation, lines 20, 22 are connected across a small potential difference. This enables a small current in the order of about 10 microamperes or less to flow between wire 18 and layer 16. As best illustrated in FIG. 1, this causes surface charges of opposite polarity to build up on wire 18 and layer 16 which, in turn, establishes an ionic balance or stability which tends to oppose the current flow. However, the flowing or stirring action of the fluid as it flows past probe 10 tends to disturb the local ordering of ions at and near wire 18 and layer 16. The disturbance causes surface charge and ordered ions to be "bled off" or transferred between at least one of either the wire 18 or layer 16, thereby permitting the current to continue flowing between wire 18 and layer 16. Thus, as disordered ions migrate or are conveyed towards the sensing elements 16 and 18 by virtue of fluid motion, the ordered ions are displaced or transferred between at least one of the wire 18 or layer 16 and the fluid, a resultant current or charge is caused to flow between the wire 18 and layer 16. It has been found that the level of such current flow is closely related to the rate of flow of fluid past the probe 10. Accordingly, an accurate measure of the flow rate is provided. Thus, current flow is directly related to the degree of local ionic order or disorder at or near the wire 18 or layer 16.

It will be appreciated that the illustrated apparatus and method is very useful for monitoring all types of fluid flow, such as fluid flowing in a vessel. In particular, it is very useful for monitoring, for example, blood flow in a blood vessel 11 (FIG. 5) upstream and downstream from a region of occlusion. While the volume flow rate of blood upstream and downstream from the occlusion 13 must be the same when averaged over a pumping cycle, the pressure variations upstream of the occlusion 13 cause a circulating localized blood flow which is sensed by the probe 10. Depending upon the amount of blockage caused by the occlusion 13, the downstream flow rate may be substantially reduced in comparison to the upstream flow rate.

FIG. 3 illustrates the current which may be expected from the probe 10 when there is little or no blockage (waveform 30) and when there is blockage (waveform 32) caused, for example, by an occlusion 13. Waveform 30 is characterized by a relatively large current flow which is well modulated by coronary pumping. In contrast, waveform 32 depicts a substantially reduced rate of change in velocity and pressure which, in turn, provides an indication of the blood flow rate. The probe 10 measures a current having substantially less magnitude and modulation.

A current sensing circuit or electrical circuit 15 for supplying current to probe 10 and recording the responsive reaction to a flowing fluid stream is illustrated in FIG. 4. Specific identifications for the illustrated components are set forth in Table I.

TABLE I

| REFERENCE NUMERAL | IDENTIFICATION |
|---|---|
| 40 | 25 K |
| 42 | 25 K |
| 44 | 7.8 K |
| 46 | 2N4117T |
| 48 | 5 K |
| 50 | 2N2222A |
| 52 | 30 K |
| 54 | 0.1 micro farad |
| 56 | 10 K |
| 58 | 1/2 LT 1078 |
| 60 | 0.1 micro farad |
| 62 | 51 K cermet, 3-1/2 turn |
| 64 | 51 K |
| 66 | 1/2 LT 1078 |
| 68 | 51 K |

In the example illustrated in FIG. 4, probe 10 is inserted into one arm of a bridge arrangement; the other arms comprising resistors 40, 42 and 44. Resistors 40 and 42 have an equal value, so that the potential difference across nodes 41, 43 is proportional to the difference in the current flowing through those resistors. Resistor 44 has a resistance which will cause a nearly equal, but different, current flow through resistors 40, 42 and thus maintain a small potential across nodes 41, 43.

The output potential across nodes 41, 43 is applied to the input side of differential amplifier 66. Differential amplifier 66 has a conventional feedback path through resistor 68 and back to an active terminal 66a. A small current flows through this path and into node 43. Thus, a current flows through probe 10 which is the sum of the currents through resistors 40 and 68.

The current for resistor 44 and probe 10 is supplied by a current source 70 coupled to the bridge at node 47. In the embodiment being described, the current source 70 comprises transistor 50, resistor 52, capacitor 54 and potentiometer 56. In the embodiment being described, the current source 70 provides a current of approximately 10 microamperes or less. This relatively small driving current is advantageous because it does not expose, for example, either a user of the probe 10 or a patient to an undesirable level of current. Also, sensors 19 and 20 may be used in a side-by-side manner for providing multiple sensing signals, colorimetry, spectrophotometry, fluorescent, analytical qualitative and quantitative analysis.

A current sink or drain 75 is coupled to the bridge at node 49. The current drain 75 comprises a field effect transistor 46 and resistor 48.

A reference potential for differential amplifier 66 is provided by a variable potential source 78 comprising potentiometer 62, capacitor 60, differential amplifier 58 and resistor 64. Potentiometer 62 is adjusted to supply a reference potential. The reference potential may be charged, thereby permitting the operator to establish a desired reference level for the final output from differential amplifier 66, such as zero. For example, the operator may adjust potentiometer 62 to compensate for system offset and establish a reference level of zero. The output signal from differential amplifier 66 is supplied on line 79 to a suitable monitor or display 8d (FIG. 1) such that graphical representation 8g may be produced.

The potential applied on line 79 to monitor 80 is proportional to the current flow through probe 10, as described above and as illustrated by waveforms 30 and 32 of FIG. 3. Thus, monitor 80 will display a trace corresponding to variations in the speed or flow rate of the fluid flowing past probe 10.

It will be appreciated that the current applied to probe 10 may be servo-controlled, modulated, encoded or otherwise modified. Furthermore, the technique of this invention may be used to measure the flow of a wide range of conductive, ionic, electrolytic or dielectric solutions. For use in applications wherein fluid flow speed must be accurately measured or carefully controlled, the circuit of FIG. 4 may be easily calibrated. Calibration simply involves placing probe 10 in a reference solution flowing at a reference speed and then recording the output from differential amplifier 66. Output values may be recorded for a series of reference solutions and over a range of different speeds for storage in tabular form, for example, in the computer 67 (FIG. 1). Subsequently, actual measurements may be taken and compared to the predetermined rate and the difference therebetween displayed on monitor 80.

A method for measuring flow rate of a fluid in a vessel will now be described. For purposes of illustration only, the method will be described as it may be used for measuring flow rate of blood in a vessel 11 (FIG. 5) around occlusion 13. As best shown in FIG. 5, probe 10 is inserted into vessel 11 in blood at or near the point of occlusion 13 so that the wire 18 and layer 16 are positioned near occlusion 13. For this purpose, it may be desired to place the probe 10 on the end of a catheter (not shown). The circuit 15 is then energized with a small current on the order of about 10 microamperes or less by current source 70. In the manner described earlier herein, circuit 15 measures the transfer or displacement of ordered layers of ions between one or more of the conductive surfaces (wire 18 and layer 16) and the blood. The circuit 15 generates a signal on line 79 corresponding to the measurement obtained. The signal is then displayed on monitor 80 (FIGS. 1 and 4) to give the user a waveform corresponding to the flow rate of the blood near the occlusion 13.

In the example being described, the probe 10 may first be positioned upstream of the occlusion 13, as shown in FIG. 5. Because of the relatively small size of the probe 10 relative to the vessel 11 and depending on the size of the occlusion 13, the probe 10 may then be moved until the wire 18 and layer 16 are positioned downstream of the occlusion 13. Another measurement representing the fluid flow rate downstream of the occlusion 13 may then be taken. The upstream and downstream flow measurements can subsequently be compared to provide accurate information about the flow rate past the occlusion 13, the size of the occlusion 13, and the amount of blockage caused by the occlusion 13. Once all desired measurements have been taken, the probe 10 may be removed from the vessel 11.

Referring to FIGS. 8 and 9, it should be understood that probe 10 could be configured such that two identical circuits (not shown) can be used with a single probe 10 having a plurality of conductors for generating multiple signals. The set of conductors 16 and 18 comprises a common ground and two conductors which may be individually coupled to their own sensing circuit 15 or to conventional switching circuitry (not shown) which would permit a single circuit 15 to be used with the conductors 16 and 18. For example, referring to FIG. 4, mode 43 or mode 47, but not both, could be common to the "shared" electrode. The outputs from the identical circuits would either be isolated or pass through a sufficiently high value current limiting resistance which may be applied to a suitable high impedance input device so as to render current leakage between the two circuits negligible. It should be appreciated that this isolation may not be required in all applications. Using a probe 10 which is capable of generating separate measurement signals representing fluid flow rate permits an upstream and downstream measurement to be taken without having to re-position the probe 10. When configured with two pairs of conductors 16 and 18 which are separated by a distance X (FIG. 8) as shown, the upstream and downstream flow measurements mentioned above to be taken without moving the probe 10.

Figure 6:
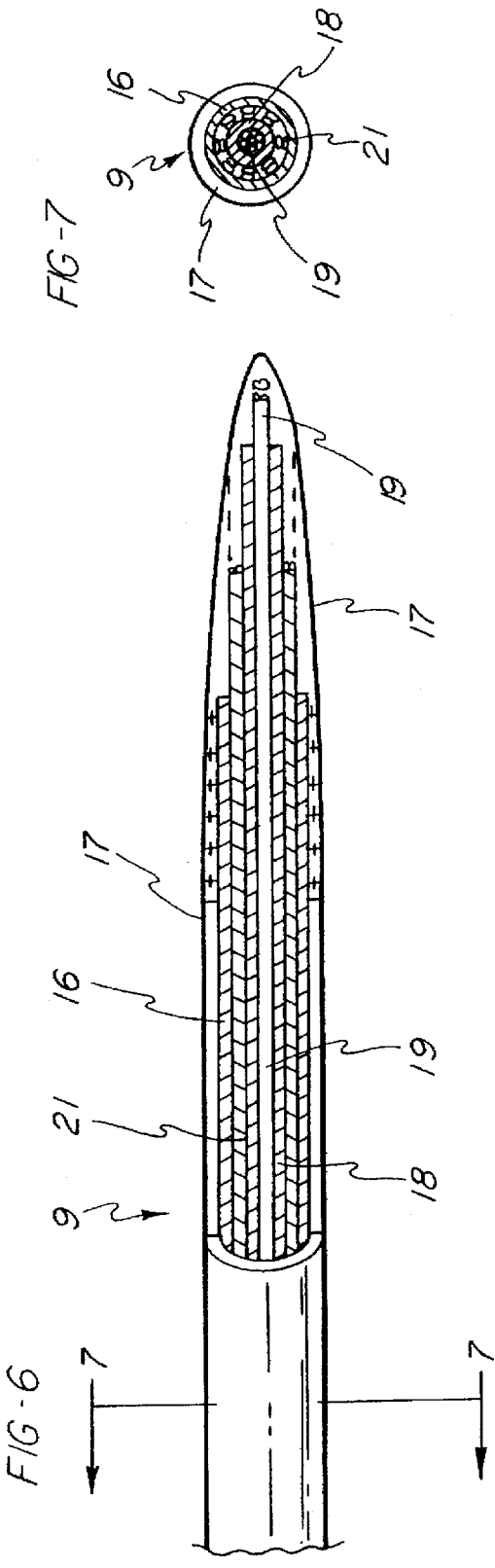
FIG. 6 is a fragmentary view showing the flow meter having an optical sensor.

Another embodiment is shown in FIG. 6 wherein the flow measuring system and method further comprises an optical sensor 19. The probe 9 illustrated in FIG. 6 comprises a first optical sensor 19, around which the conductor or wire 18 is placed. A second optical sensor 21 is then positioned around wire 18 and surrounded by the conductor or layer 16. Finally, an insulator, such as protective coating 17, is then molded over layer 16.

The probe 9 permits flow measuring as described herein, regarding probe 10, but probe 9 also permits optical sensing which may be useful for visually inspecting, for example, an occlusion or a wall of an artery if the probe 9 is used in a medical application. The sensors 19 and 21 could comprise a plurality of optical fibers as shown. Note that sensor 21 could be used for illumination while sensor 19 is used for visual inspection or imaging.

The probe 9 shown in FIG. 6 may be coupled to flow meter 8 such that computer 8a can control the operation of the probe 9 and the information transmitted thereto or received therefrom.

Although the example above has been described in connection with measuring blood flow in a blood vessel, it should be appreciated that the method and apparatus of this invention has been found to be effective when measuring flow rates of other types of fluids. For example, it may be used to measure the flow rate of viscous fluids, such as syrup in a beverage dispensing machine.

In addition, it should be appreciated that this method and apparatus could also be used in conjunction with other medical instruments. For example, it could be integrally formed with a balloon catheter, thereby providing means for generating flow measuring and optical feedback information during an angioplasti procedure.

While the method herein described, and the form of apparatus for carrying this method into effect, constitute a preferred embodiment of this invention, it is to be understood that the invention is not limited to this precise method and form of apparatus, and that changes may be made in either without departing from the scope of the invention, which is defined in the appended claims.

What is claimed is:

1. A measuring device for measuring blockage caused by an occlusion in a blood vessel comprising:
    a probe for placing in the vessel near the occlusion, said probe having a pair of conductors;
    a circuit coupled to said pair of conductors for generating a signal using only said pair of conductors, said signal corresponding to the movement of ions as blood flows past said probe as ions are replenished to said pair of conductors; and
    a display coupled to said circuit for receiving said signal and generating a display corresponding indicating a size of the occlusion.

2. The measuring device as recited in claim 1 wherein said circuit comprises a bridge, a current source, a current drain and an operational amplifier which are operatively coupled together and to said at least two conductors to enable said circuit to generate said signal.

3. The measuring device as recited in claim 1 wherein said probe comprises a pair of conductors which have a spacing therebetween of not more than 10 mm.

4. The measuring device as recited in claim 1 wherein said at least two conductors each have a protective coating.

5. The measuring device as recited in claim 4 wherein said protective coating is Teflon.

6. The measuring device as recited in claim 1 wherein said current source provides a current of 10 microamperes or less.

7. The measuring device as recited in claim 1 wherein one of said at least two conductors comprises an outer diameter of not more than 0.15 mm or less.

8. The measuring device as recited in claim 1 wherein said probe has two pairs of conductors.

* * * * *